US009052494B2

(12) United States Patent
Hwang et al.

(10) Patent No.: US 9,052,494 B2
(45) Date of Patent: Jun. 9, 2015

(54) OPTICAL IMAGING SYSTEM WITH CATOPTRIC OBJECTIVE; BROADBAND OBJECTIVE WITH MIRROR; AND REFRACTIVE LENSES AND BROADBAND OPTICAL IMAGING SYSTEM HAVING TWO OR MORE IMAGING PATHS

(75) Inventors: Shiow-Hwei Hwang, San Ramon, CA (US); Gregory L. Kirk, Pleasanton, CA (US); Hwan J. Jeong, Los Altos, CA (US); David Shafer, Fairfield, CT (US); Russel Hudyma, San Ramon, CA (US)

(73) Assignee: KLA-Tencor Technologies Corporation, Milptas, CA (US)

( * ) Notice: Subject to any disclaimer, the term of this patent is extended or adjusted under 35 U.S.C. 154(b) by 1327 days.

(21) Appl. No.: 12/750,488

(22) Filed: Mar. 30, 2010

(65) Prior Publication Data
US 2011/0242528 A1 Oct. 6, 2011
US 2013/0155399 A9 Jun. 20, 2013

Related U.S. Application Data

(63) Continuation of application No. PCT/US2008/078493, filed on Oct. 1, 2008.

(60) Provisional application No. 61/000,254, filed on Oct. 24, 2007, provisional application No. 60/997,306, filed on Oct. 2, 2007.

(51) Int. Cl.
*G01N 21/00* (2006.01)
*G02B 17/08* (2006.01)
(Continued)

(52) U.S. Cl.
CPC .......... *G02B 17/084* (2013.01); *G01N 21/9501* (2013.01); *G03F 1/84* (2013.01)

(58) Field of Classification Search
CPC .......... G01N 21/9501; G01N 21/8806; G01N 21/956
USPC ........... 356/237.2, 237.5, 237.1; 35/730, 365, 35/676; 359/730, 365, 676
See application file for complete search history.

(56) References Cited

U.S. PATENT DOCUMENTS 4,088,397 A 5/1978 Jourdan et al.
5,999,310 A 12/1999 Shafer et al.
(Continued)

FOREIGN PATENT DOCUMENTS

DE 102005042005 A 7/2006
JP 2000221405 A 8/2000
(Continued)

OTHER PUBLICATIONS

European Supplementary Search Report issued date Oct. 30, 2012 for European Patent Application No. EP 08835721.
(Continued)

*Primary Examiner* — Kara E Geisel
*Assistant Examiner* — Iyabo S Alli
(74) *Attorney, Agent, or Firm* — Joshua D. Isenberg; JDI Patent

(57) ABSTRACT

An optical system may include an objective having at least four mirrors including an outermost mirror with aspect ratio <20:1 and focusing optics including a refractive optical element. The objective provides imaging at numerical aperture >0.7, central obscuration <35% in pupil. An objective may have two or more mirrors, one with a refractive module that seals off an outermost mirror's central opening. A broad band imaging system may include one objective and two or more imaging paths that provide imaging at numerical aperture >0.7 and field of view >0.8 mm. An optical imaging system may comprise an objective and two or more imaging paths. The imaging paths may provide two or more simultaneous broadband images of a sample in two or more modes. The modes may have different illumination and/or collection pupil apertures or different pixel sizes at the sample.

47 Claims, 14 Drawing Sheets

(51) Int. Cl.
*G01N 21/95* (2006.01)
*G03F 1/84* (2012.01)

(56) References Cited

U.S. PATENT DOCUMENTS

| | | | |
|---|---|---|---|
| 6,078,386 | A | 6/2000 | Tsai et al. |
| 6,404,498 | B1 | 6/2002 | Madea et al. |
| 6,473,243 | B1 | 10/2002 | Omura |
| 6,762,831 | B2 | 7/2004 | Shibata et al. |
| 6,867,424 | B2 | 3/2005 | Kurosawa et al. |
| 6,894,834 | B2 | 5/2005 | Mann et al. |
| 7,138,640 | B1 | 11/2006 | Delgado et al. |
| 7,180,586 | B2 * | 2/2007 | Neumann et al. .......... 356/237.5 |
| 7,351,980 | B2 | 4/2008 | Lange |
| 7,382,498 | B1 | 6/2008 | Cook |
| 7,682,031 | B2 | 3/2010 | Mann et al. |
| 8,004,755 | B2 | 8/2011 | Mann et al. |
| 8,317,345 | B2 | 11/2012 | Mann et al. |
| 2002/0044260 | A1 | 4/2002 | Takahashi et al. |
| 2005/0052643 | A1 | 3/2005 | Lange et al. |
| 2005/0062962 | A1 | 3/2005 | Fairley et al. |
| 2006/0219930 | A1 | 10/2006 | Lange |
| 2006/0280498 | A1 | 12/2006 | Souma et al. |

FOREIGN PATENT DOCUMENTS

| | | |
|---|---|---|
| JP | 2001517806 | 10/2001 |
| JP | 2002083766 A | 3/2002 |
| JP | 2003161886 A | 6/2003 |
| JP | 2003527636 A | 9/2003 |
| JP | 2005164839 A | 6/2005 |
| JP | 2006343554 A | 12/2006 |
| JP | 2007527545 | 9/2007 |
| WO | 9908134 A | 2/1999 |
| WO | 0039623 A | 7/2000 |
| WO | 0169298 A | 9/2001 |
| WO | 03016977 A | 2/2003 |
| WO | 2005026782 | 3/2005 |
| WO | 2009046137 | 4/2009 |

OTHER PUBLICATIONS

International Search Report mailed date Jan. 30, 2009, issued for International Application No: PCT/US2008/078493.

International Pre! JMIN ARY Report on Patentability and Written Opinion of the International Searching Authority mailed date Apr. 15, 2010 issued for PCT International Application No. PCT/US2008/078493.

U.S. Appl. No. 60/997,306, filed Oct. 2, 2007.

U.S. Appl. No. 61/000,254, filed Oct. 24, 2007.

Japanese Office Action mailed date Feb. 12, 2013, issued for Japanese Patent Application No. JP 2010-528110.

Japanese Office Action for JP Application No. 2013-156941, dated Apr. 15, 2014.

* cited by examiner

|   | Radius | Thickness | Glass | Aperture (half dia) |
|---|---|---|---|---|
|   |   | 10.000 |   | 1.0 |
| M 4 | -207.69849 | 94.147 | Reflect | 21.6 |
| M 3 | 274.08664 | -94.147 | Reflect | 125.0 |
|   |   | 94.147 |   |   |
|   |   | 16.600 |   | 24.7 |
|   |   | 5.400 |   | 11.8 |
|   |   | 239.854 |   | 8.5 |
| M 2 | -260.068 | -239.854 | Reflect | 198.4 |
| M 1 | -164.274 | 239.854 | Reflect | 37.6 |
|   |   | 1163.175 |   | 39.4 |

|   | K | A | B | C | D | E | F | G | H | J |
|---|---|---|---|---|---|---|---|---|---|---|
| Asphere 4 | -0.193 | 0 | -3.110E-13 | -3.669E-17 | 1.957E-21 | -1.304E-26 | -2.835E-29 | 2.609E-33 | -9.944E-38 | 1.312E-42 |
| Asphere 3 | -1.347 | 0 | -3.073E-13 | -5.883E-17 | 7.013E-21 | -1.502E-24 | 2.165E-28 | -2.181E-32 | 1.161E-36 | -2.329E-41 |
| Asphere 2 | -0.010 | 0 | 2.430E-15 | 2.141E-19 | -1.088E-23 | 3.911E-28 | -3.481E-33 | -1.158E-37 | 3.144E-42 | -2.272E-47 |
| Asphere 1 | 13.333 | 0 | 6.920E-12 | 4.122E-14 | -4.662E-17 | 5.870E-20 | -2.870E-23 | -5.090E-27 | 1.493E-29 | -4.875E-33 |

FIG. 1c

|  | Radius | Thickness | Glass | Diameter |
|---|---|---|---|---|
|  |  | 400.000 |  | 68.9 |
| M 1 | 73.022 | -380.857 | Reflect | 31.0 |
| M 2 | 398.435 | 380.857 | Reflect | 350.0 |
|  |  | 20.000 |  | 4.4 |
|  |  | 107.410 |  | 20.0 |
| M 3 | 1000.778 | -107.410 | Reflect | 124.0 |
| M 4 | 158.200 | 107.410 | Reflect | 240.0 |
|  |  | 22.000 |  | 20.6 |
|  |  | 157.814 |  | 57.6 |
| M 5 | -366.332 | -76.290 | Reflect | 400.1 |
| Stop |  | -81.523 |  | 412.7 |
| M 6 | 303.237 | 157.814 | Reflect | 416.0 |
|  |  | 12.000 |  | 1.5 |

|  | K | A | B | C |
|---|---|---|---|---|
| Asphere 1 | 2.289 | 0.000 | 1.265E-09 | -1.663E-12 |
| Asphere 2 | -0.022 | 0.000 | 4.127E-15 | -4.455E-20 |
| Asphere 3 | 183.527 | 0.000 | -4.204E-12 | 2.179E-15 |
| Asphere 4 | 0.376 | 0 | -2.885E-13 | -8.133E-18 |
| Asphere 5 | -1.359 | 0 | 1.149E-14 | -1.233E-19 |
| Asphere 6 | -1.368 | 0 | 4.375E-14 | -3.138E-19 |

FIG. 2c

|  | Radius | Thickness | Glass | Diameter |
|---|---|---|---|---|
|  |  | 8.500 |  | 1.5 |
|  |  | 134.367 |  |  |
| M 6 | -233.323 | -61.740 | Reflect | 336.1 |
| stop |  | -72.628 |  |  |
| M 5 | 329.905 | 134.367 | Reflect | 317.6 |
|  |  | 21.714 |  | 40.2 |
|  |  | 107.766 |  | 22.4 |
| M 4 | -180.837 | -107.766 | Reflect | 208.7 |
| M 3 | -501.603 | 104.266 | Reflect | 113.4 |
|  |  | 18.500 |  | 12.5 |
|  |  | 378.287 |  |  |
| M 2 | -402.604 | -378.287 | Reflect | 360.0 |
| M 1 | -99.961 | 378.287 | Reflect | 37.4 |
|  |  |  |  | 1.5 |

|  | K | A | B | C | D | E |
|---|---|---|---|---|---|---|
| Asphere 6 | -1.3539 | 0 | -1.441E-13 | -8.338E-19 | 0 | 0 |
| Asphere 5 | -3.0285 | 0 | -6.570E-14 | 7.538E-19 | 0 | 0 |
| Asphere 4 | 0.3561 | 0 | 8.172E-14 | 9.200E-19 | 0 | 0 |
| Asphere 3 | 0.0000 | 1.756E-07 | 1.305E-11 | -3.517E-15 | -8.901E-19 | -1.085E-22 |
| Asphere 2 | -0.0364 | 0 | -2.093E-15 | 1.287E-20 | 0 | 0 |
| Asphere 1 | 7.0385 | 0 | -4.884E-10 | 5.552E-13 | 0 | 0 |

FIG. 2f

OPTICAL IMAGING SYSTEM WITH CATOPTRIC OBJECTIVE; BROADBAND OBJECTIVE WITH MIRROR; AND REFRACTIVE LENSES AND BROADBAND OPTICAL IMAGING SYSTEM HAVING TWO OR MORE IMAGING PATHS

CLAIM OF PRIORITY

This application claims the priority benefit of U.S. Provisional Patent Application No. 60/997,306,filed Oct. 2, 2007, the entire disclosures of which are incorporated by reference herein. This application also claims the priority benefit of U.S. Provisional Patent Application No. 61/000,254,filed Oct. 24, 2007,the entire disclosures of which are incorporated by reference herein.

This application is a continuation of International application No. PCT/US2008/078493 filed Oct. 1, 2008. International application No. PCT/US2008/078493 claims the benefit of US provisional patent application No. 60/000,254 filed Oct. 24, 2007. International application No. PCT/US2008/078493 claims the benefit of U.S. provisional patent application No. 60/997,306 filed Oct. 2, 2007.

FIELD OF THE INVENTION

This invention relates to imaging optics for sample inspection, and in particular to the use of catoptric objectives, catadioptric objectives, and the use of multiple wavelength bands and/or inspection modes simultaneously.

BACKGROUND OF THE INVENTION

Defect inspection for the DUV range is currently being performed with all-refractive objectives or with catadioptric (combination of refractive and reflective) objectives. For wavelengths shorter than DUV, US Patent publication 2006/0219930 proposes the use of an all-reflective, or catoptric, optical system. US patent publication 2006/0219930 (now U.S. Pat. No. 7,351,980) is hereby incorporated by reference in its entirety.

As design rules shrink in integrated circuit technology, one way to improve the detection of smaller defects is to increase the resolution of the optical inspection system by utilizing shorter wavelengths. However, as the wavelength goes below 250 nm, the dispersion characteristics of the available optical material such as fused silica and $CaF_2$ increases significantly. Furthermore, the availability of manufacturable Anti-Reflective (AR) coating materials effective over the spectrum from sub-200 nm to above 400 nm wavelength is limited. (Good AR coating for a reflective microscope is essential to minimize flare, stray light, etc). These conditions make it extremely difficult to design and manufacture an all-refractive or catadioptric optical system that supports broadband illumination and detection including wavelengths shorter than 250 nm.

The all-reflective optical system proposed in US patent publication 2006/0219930 (now U.S. Pat. No. 7,351,980) provides substantial improvements in manufacturability and design of an optical system for use in wafer inspection with broadband illumination including wavelengths below 250 nm. Furthermore, the design of the objective in U.S. Pat. No. 7,351,980 includes an opening in the mirror adjacent to the wafer that is being inspected. The presence of the opening presents a potential risk of deposition of contaminants onto the wafer and/or diffusion of contaminations into the objective. Such contamination risks are undesirable in wafer inspection systems. One could reduce contamination risk by providing a large flow through the opening that is presented by an all reflective optical design. However, this creates mechanical instabilities at or near the opening. U.S. Pat. No. 7,138,640 describes a method for protecting optical components using a gas purge system that blocks contaminants from reaching the optical surfaces of optical components and transports contaminants away from those surfaces. However, it may be difficult to implement this method in a broadband system that includes wavelengths below 200 nm due to color correction, AR performance issues and or mechanical instability if the window is made too thin.

The prior art describes a number of sample inspection systems that have various other disadvantages. For example, U.S. Pat. No. 6,867,424 describes an optical system in which there is only a single imaging path preventing simultaneous usage of two light sources with different modes.

U.S. Pat. No. 7,359,044 describes the use of laser-based illumination (as opposed to broadband illumination) for bright field and dark field imaging in a sample inspection system. Multiple lasers are used to provide illumination, but there is only a single imaging path.

Lange 20050052643 describes an inspection system in which there are dual illumination paths but only a single imaging path.

U.S. Pat. No. 6,404,498 also describes a system in which there are dual illumination paths but only a single imaging path.

U.S. Pat. No. 6,078,386 teaches an inspection system having dual imaging paths but uses narrow band, e.g., laser illumination and imaging. In addition, the laser beam is introduced to the sample from outside the objective. When two light sources are used, the narrow band illumination is introduced to the sample from outside the objective in a spatially coherent mode.

U.S. Pat. No. 6,762,831 teaches a sample inspection system that uses narrow band illumination with DUV and VUV radiation introduced to a sample through the objective. Illumination through the objective enables spatially incoherent illumination modes. Illumination and imaging are done with light of two different wavelengths generated by two lasers.

It is within this context that embodiments of the present invention arise.

SUMMARY OF THE INVENTION

According to an embodiment of the invention, an optical system for sample inspection may comprise an objective having at least four mirrors including an outermost mirror and focusing optics optically coupled to the objective. The focusing optics include one or more refractive optical elements. The objective is configured to provide imaging at a numerical aperture greater than 0.7,central obscuration less than 35% in pupil. An aspect ratio of outermost mirror at a sample side is no more than 20:1.

In certain embodiments of the present invention, an outermost mirror of an objective for an imaging system such as a wafer inspection system may have improved manufacturability by decreasing its aspect ratio at a sample side to between about 10:1 and about 20:1. This allows inspection with a more manufacturable objective of high Numerical Aperture (NA), greater than 0.7,with large Field of View (FOV), greater than 0.5 mm, low central obscuration (e.g., less than 35%, less than 30% or less than 25%), broadband spectrum below 250 nm, and requiring no more than 6 mirrors. Such a system may further utilize one or more refractive elements in the pupil relay and imaging optics external to the objective, in order to improve the system flexibility and efficiency. The refractive elements in the pupil relay and imaging optics minimize the constraints on the packaging, and create the opportunity for aberration compensation to the objective, thereby lowering the tolerance requirements. According to one embodiment, the objective may be a 4 mirror objective. Another embodiment of the invention may utilize a 6 mirror objective. Both embodiments have more manufacturable outermost elements, with two configurations thereof A refractive pupil relay that can be modified to be used with either of the two embodiments of the inventive objective is also disclosed.

Additional embodiments of the present invention improve upon the manufacturability, photo-contamination control, optical performance and wafer edge inspection of the front element of a reflective broadband objective by providing a refractive element that closes the opening closest to the sample, thereby improving photo-contamination control (PCC). Some embodiments of the present invention utilize a refractive optical module in a central opening of a reflective element closest to a sample. In some embodiments of the present invention the refractive optical element is a curved refractive shell-like lens element. According to an embodiment of the present invention, an imaging objective may comprise two or more mirrors, at least one of which contains a refractive module that seals off a central opening of an outermost mirror of the two or more mirrors in order to substantially isolate an atmosphere inside the objective from a sample atmosphere.

In some embodiments, the refractive element can be less curved, and even closer to being flat. The refractive module can also consist of more than one refractive element. Embodiments of the present invention may utilize refractive optical elements to redistribute field curvature contributions from the reflective elements of the objective, thereby improving mirror manufacturability. The reflective and refractive elements in the objective may be configured such that the angle of incidence (AOI) on the refractive elements is less than about 25 degrees to reduce the complexity of the broadband anti-reflective (AR) coating and improve the achievable AR performance.

Further embodiments of this invention may provide an apparatus and method for providing simultaneous defect inspection data from multiple wavelength bands, Bright Field (BF) and Dark Field (DF), differing magnifications, and independent alignment and magnification adjustment. These features provide more efficient utilization of imaging resources, allow for simultaneous high sensitivity BF inspection and better light-budget DF inspection.

According to another embodiment, an optical imaging system may comprise a single objective and two or more broadband imaging paths optically coupled to the objective. The objective and imaging paths may be configured to provide broadband imaging at a numerical aperture greater than 0.7 and a field of view greater than 0.8 mm.

According to an alternative embodiment, an optical imaging system may comprise an objective configured to collect light from a sample located proximate the objective and two or more imaging paths optically coupled to the objective. The two or more imaging paths may be configured to provide a corresponding two or more simultaneous images of the sample in a corresponding two or more modes. Each mode of the two or more modes may be characterized by an illumination pupil aperture and/or a collection pupil aperture and wherein each of the two or more simultaneous images is a broad band image.

According to another alternative embodiment, an optical imaging system may comprise an objective configured to collect light from a sample located proximate the objective and two or more imaging paths optically coupled to the objective. The two or more imaging paths may be configured to provide a corresponding two or more simultaneous images of the sample in a corresponding two or more modes. Each mode may be characterized by a different pixel size at the sample.

According to yet another alternative embodiment, an optical imaging system may comprise a single objective and two or more imaging paths optically coupled to the objective. The imaging paths may be configured to transmit two different wavelength bands. At least one wavelength band is a broadband wavelength band having a wavelength bandwidth greater than 10 nm in width. Illumination for the two different wavelength bands is coupled to a sample through the objective wherein the objective and imaging paths are configured to provide imaging at a numerical aperture greater than 0.7 and a field of view greater than 0.8 mm.

BRIEF DESCRIPTION OF THE FIGURES

FIG. 1c sets forth an exemplary set of dimensions and specifications for the objective portion depicted in FIG. 1b.

FIG. 1d shows an example of inventive refractive focusing optics that may be used with the objective of FIG. 1b in a system of the type shown in FIG. 1a.

FIG. 2b shows an enlargement of a region of negative spherical aberration in the objective portion depicted in FIG. 2a.

FIG. 2c sets forth an example of dimensions and specifications for an objective of the type depicted in FIG. 2a.

FIG. 2d shows an example of focusing optics that may be used with an objective with flat Petzval curvature, as in FIG. 2a.

FIG. 2f depicts tables setting forth an example of dimensions and specifications for an objective of the type depicted in FIG. 2e.

DETAILED DESCRIPTION OF THE INVENTION

Figure 1A:
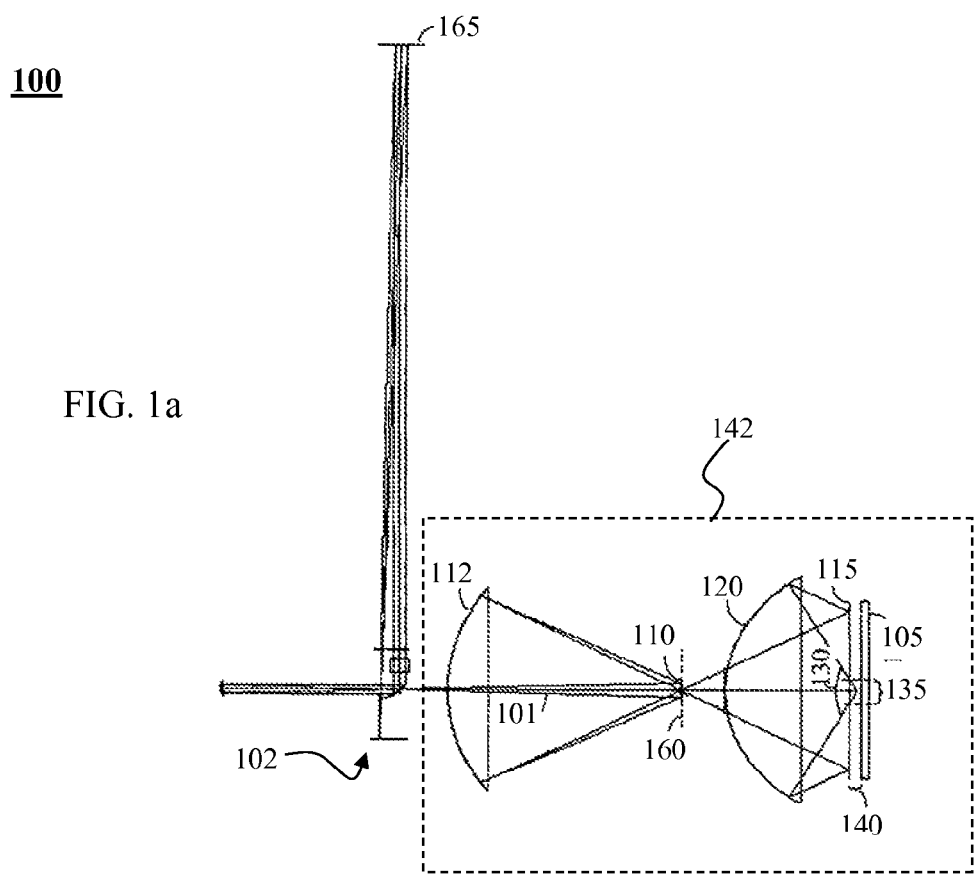
FIG. 1a depicts an optical system according to the prior art.

FIG. 1a depicts an example of an optical imaging system 100 that uses a 4-mirror objective design based on the one disclosed in US Patent publication 2006/0219930. The optical system depicted in FIG. 1a includes a pupil relay portion 102 and an objective portion 142. The objective portion 142 includes mirrors 110 (M1), 112 (M2), 115 (M3) and 120 (M4). An incident light beam 101 from the pupil relay portion 102 impinges first onto mirror 110 (M1), then mirror 112 (M2), then an outermost mirror 115 (M3), then mirror 120 (M4), then onto sample 105. The sample is generally located close to the outermost mirror 115 in a sample inspection system, such as a wafer inspection system or biological specimen inspection system or mask inspection system. The nomenclature as utilized herein may be construed as a definition of the terms denoting the relative positions of the mirrors within the example being illustrated, i.e., the numbering of the mirrors is defined by the order in which the incident light beam from the pupil relay portion 102 (and/or from an illuminator) impinges on the mirrors. For a 4-mirror objective design, the M3 mirror (the outermost mirror 115) is closest to the sample when the objective portion 142 is used in the imaging system 100. Emitted rays emerging from the sample 105 impinge on the mirrors in reverse order, i.e., impinging first on M4, then, M3, then M2 then M1. The numerical aperture (NA) for the objective design shown in FIG. 1a is defined by a collection angle 130. For a given diameter of entrance opening 135, the NA is increased as the distance 140 between the outermost mirror 115 and sample 105 is decreased. A first intermediate image plane 160, interior to the objective portion 142, and a second intermediate image plane 165, external to the objective portion, are shown.

According to some, but not all embodiments of the present invention, a refractive optical element such as a lens may be inserted into the opening 135 through M3 near the sample, as a physical barrier to photocontamination of the sample. The objective would in this case be catadioptric, i.e., containing both reflective and refractive elements.

Figure 1B:
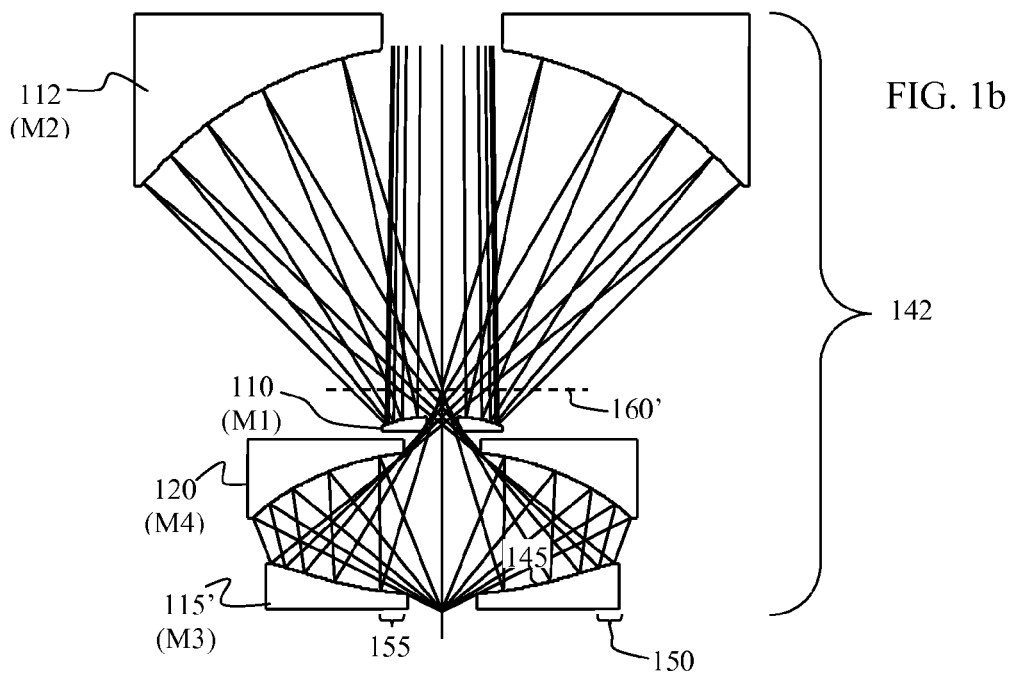
FIG. 1b depicts a first example of a four-mirror objective portion of the inventive optical system according to an embodiment of the present invention.

The objective design depicted in FIG. 1a appears from the curvature of the four mirrors to follow the generally utilized system constraint that the total Petzval curvature is close to zero for best full-field imaging quality. This constraint results in the requirement of a convex or substantially flat outermost mirror element 115. However, to achieve low central obscuration, the outermost mirror 115, i.e., the first mirror element adjacent to the external field plane at the high NA side, needs to be very close to the sample and very thin, so that the opening required to transmit the large angle cone of light can be limited in size. These two conditions, i.e., the convex or flat outermost mirror element 115 and its closeness to the sample, result in an outermost mirror element with a high aspect ratio. As used herein, the aspect ratio refers to a ratio of the diameter of the mirror to its edge thickness. A trade-off therefore results, since a very thin mirror with high aspect ratio is difficult to manufacture. By way of example, in embodiments of the present invention, the aspect ratio of the outermost mirror 115' may be less than about 20:1,e.g., between about 10:1 and about 20:1. FIG. 1b depicts the objective portion 142 of according to an alternative embodiment of the inventive optical system, which comprises a 4 mirror objective. An aspect of this first embodiment is improved manufacturability of the outermost mirror 115', which is denoted M3 viewed from the long conjugate side. The outermost mirror 115' has a curved inner surface 145, resulting in a thicker outer region 150, although the central region 155 remains thin. NA therefore need not be sacrificed. An exemplary set of dimensions and specifications for this first embodiment is listed in FIG. 1c. First intermediate image plane 160' is within objective portion 142. A second intermediate image plane (similar to image plane 165 in FIG. 1a) is external to objective portion 142.

The thicker, curved outermost mirror 115' results in several effects:

1. Improved manufacturability of the mirror and lowered cost compared to a flat, high aspect ratio mirror;
2. The Petzval curvature of the system becomes negative. (the exemplary design disclosed herein has Petzval curvature of about −80 mm) Again, a system such as the present system which allows the Petzval curvature to float to a negative value has some advantages relative to the system constrained to a near-zero Petzval curvature. Though custom design of pupil relay components may be required, the loosening of the general constraint that the Petzval curvature be near zero enables better correction of aberration, or if aberration is held constant, allows for increased FOV. Petzval curvature and radius and its relation to reflective and refractive elements is described in Warren J. Smith, "*Modern Lens Design*" McGraw-Hill, Inc., 1992,Chapter 16: Mirror and Catadioptric Systems (page 271).
3. A curvature of second intermediate image plane results; further optical correction, i.e., by relay optics, is required to map the curved intermediate image plane onto a flat final image plane. These additional relay optics required to correct for the field curvature result in a smaller accessible pupil. There are tradeoffs regarding flat vs. curved intermediate image plane (IIP): a flat IIP makes it easier to produce a larger accessible pupil, which can be advantageous if components are to be placed there. However, the smaller accessible pupil associated with a curved intermediate image plane can be advantageous in that it can be easier to shield, and also can result in a more compact system.

Figure 1D:
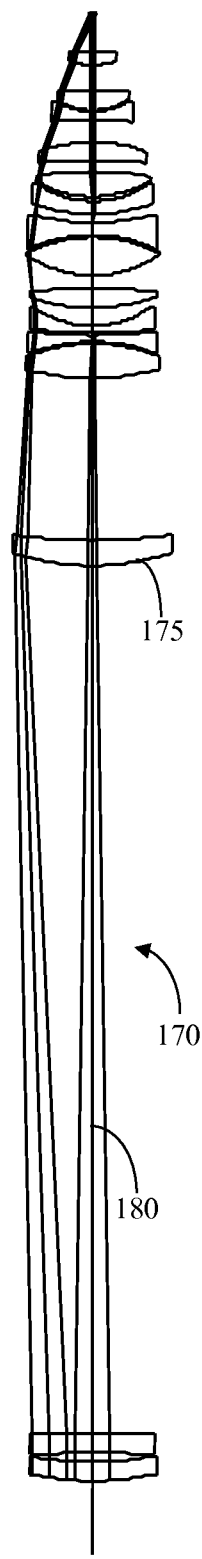

In some embodiments, the size of the outermost mirror 115' and the central obscuration may be further optimized by allowing for a curved field with a refractive pupil relay. In general, the optical power of the pupil relay needs to be sufficiently large to accommodate the Petzval curvature from the objective. FIG. 1d shows an example of a possible configuration for the pupil relay portion 102 that may be used with an objective of the type shown in FIG. 1b that has a curved Petzval curvature. The pupil relay portion 102 is external to objective portion 142. An aspect of one embodiment of the inventive optical system is the use of refractive lenses to form a pupil relay/variable magnification system, such as 170 and variable magnification imaging systems, which maps the curved intermediate image plane resulting from the negative Petzval curvature onto a flat final image plane. In addition to refractive lens elements 175, the magnification system may comprise folding mirrors and/or beam splitters. This is in contrast to the all-reflective pupil relay optics disclosed in US Patent publication 2006/0219930 (now U.S. Pat. No. 7,351, 980).

The use of refractive pupil relay optics provides a straightforward, easy correction of the curved second intermediate image plane, allowing mapping onto a flat final image plane. It is known that use of mirrors as optical elements causes Petzval numbers to tend negatively, whereas use of refractive lenses as optical elements causes Petzval numbers to tend positively, as described in the cited reference by Smith. Combining mirrors and lenses as described herein tends to easily cancel out the negative and positive Petzval numbers, to yield a flat final image plane.

An additional advantage to using refractive pupil relay optics is that the pupil relay can be centered on the optical axis 180, as shown in FIG. 1d. In contrast, pupil relay optics composed of mirrors must be moved off-axis to prevent obscuration. Off-axis mirror designs are very difficult to manufacture and to align. Though mirrors may be used for any wavelength light, we have found that lenses have sufficient bandwidth for our purposes, especially if the collection light is split out into two bands.

Figure 2A:
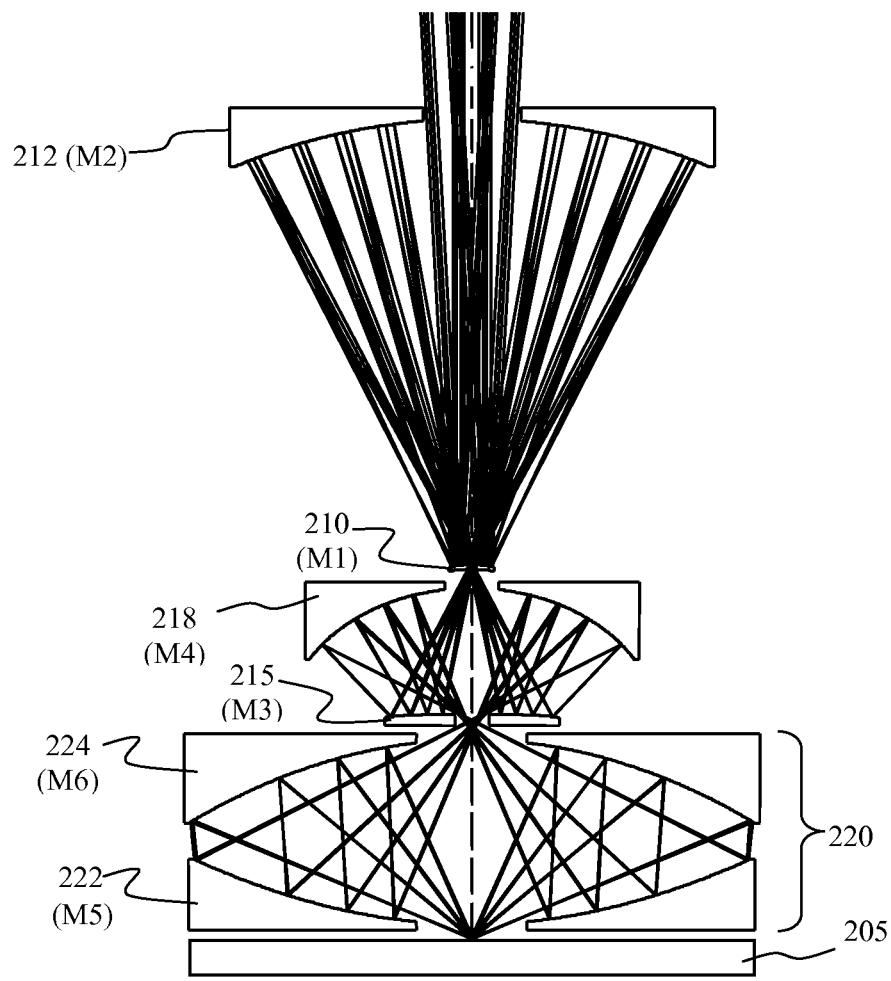
FIG. 2a illustrates a second example of a six-mirror objective portion of the optical system according to an embodiment of the present invention.
Figure 2B:
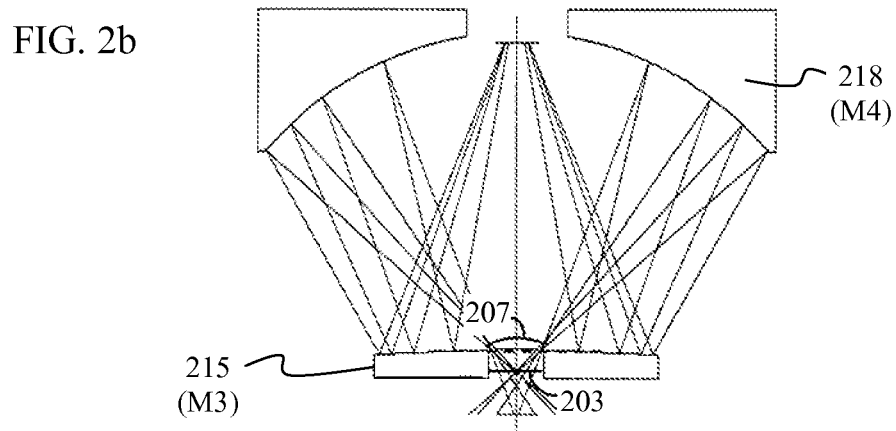

Other variations on the optical systems described above may be implemented. For example, if a flat intermediate image plane is desired, as for any of the reasons described above, a flat (or nearly flat) M3 mirror 115 may be necessary. In order to improve manufacturability of this mirror, the aspect ratio may be decreased. To implement this, an inventive configuration illustrated in FIG. 2a and FIG. 2b adds a 2-mirror relay group to an objective of the type shown in FIG. 1b. As seen in FIG. 2a and FIG. 2b an example of another alternative embodiment of the inventive objective portion of an optical system that utilizes convex mirrors 210 (M1), 215 (M3) and four concave mirrors 212 (M2), 218 (M4), 222 (M5), 224 (M6). An outermost mirror 222 may have an optional refractive element that covers a central opening, as discussed above. Mirrors 222 and 224 form a relay group 220. The relay group 220 may have a magnification, which is approximately equal to 1. In addition, the relay group 220 may be designed to introduce a slight negative spherical aberration. In one implementation, the relay group 220 may have a slight negative spherical aberration that is be less than twice the spacing between the top (reflective) surfaces of adjacent mirrors 215 (M3) and 224 (M6). With the resulting increase in the possible substrate thickness of the convex mirror 215, its aspect ratio can be decreased to a more manufacturable level. An example of dimensions for the elements of the objective shown in FIG. 2a and FIG. 2b is presented in FIG. 2c.

In the example illustrated in FIG. 2a the imaging is of infinite conjugate and has a flat Petzval field. As stated earlier, the aspect ratio of the M3 element may be large due to the fact that it needs to be placed very close to the external field plane, i.e., the plane of the sample 205, and thus the mirror element can't have a thick substrate. One remedy to improve the aspect ratio is to relay the external field to an intermediate image plane that has significant negative spherical aberration. An enlargement of the region of negative spherical aberration is shown (reversed from FIG. 2a), in FIG. 2b. This negative spherical aberration will essentially push the zonal image plane 203 from the high angular cone 207 closer to the reflective surface of convex mirror element 215 (M3). Since the plane of the sample is no longer constrained to be close to the mirror element due to the added relay, this will allow us to increase the thickness of the mirror without the need of a larger opening to accommodate the light from the large NA. Referring again to FIG. 2a, the addition of an extra two mirror relay unit 220 having outermost mirror 222 and mirror 224 within the objective portion of the system provides a way to improve manufacturability of M3 mirror 215 by decreasing its diameter, while at the same time allowing adjustment of the Petzval curvature of the intermediate image plane as follows.

Figure 2D:
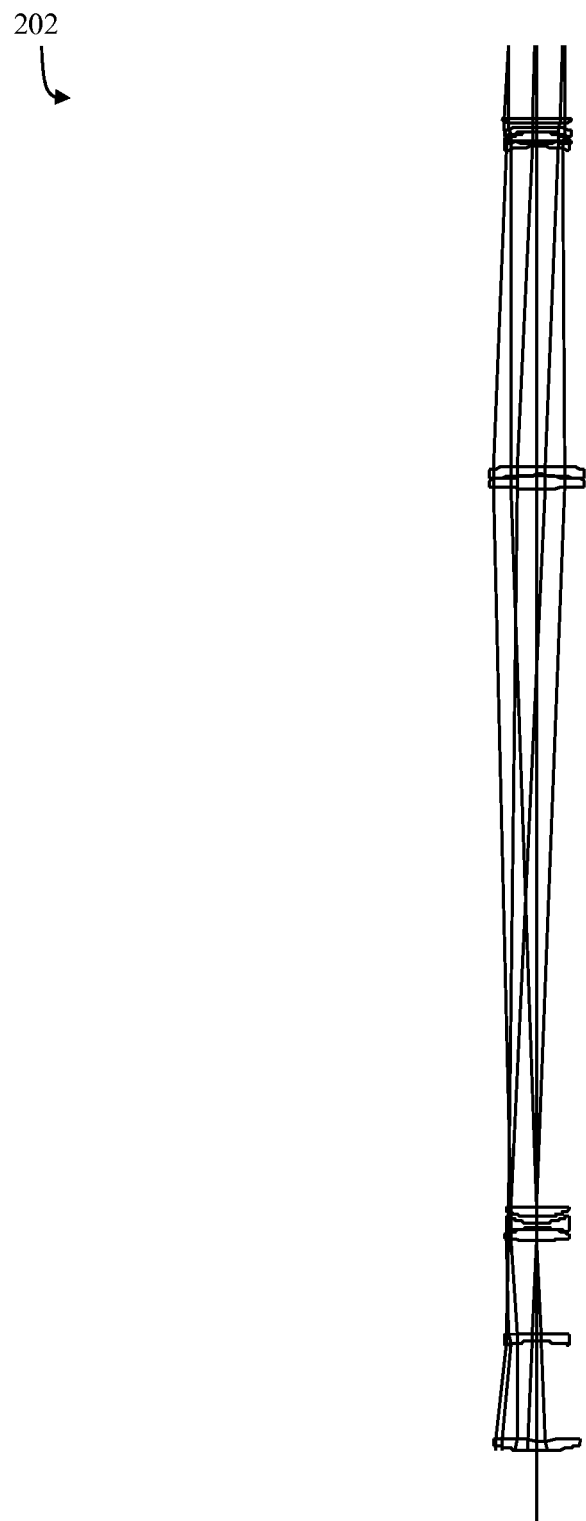

FIG. 2d shows an example of pupil relay optics 202 that may be used with an objective with flat Petzval curvature, as in FIG. 2a. The advantages over reflective pupil relay/variable magnification optics include the avoiding of off-axis and hard-to-manufacture elements. However, the spectrum bandwidth may be limited by what is practical for the anti-reflective (AR) coating. Anti-reflective coatings used with refractive elements are generally higher efficiency than high-reflective coatings used with reflective elements.

Figure 2E:
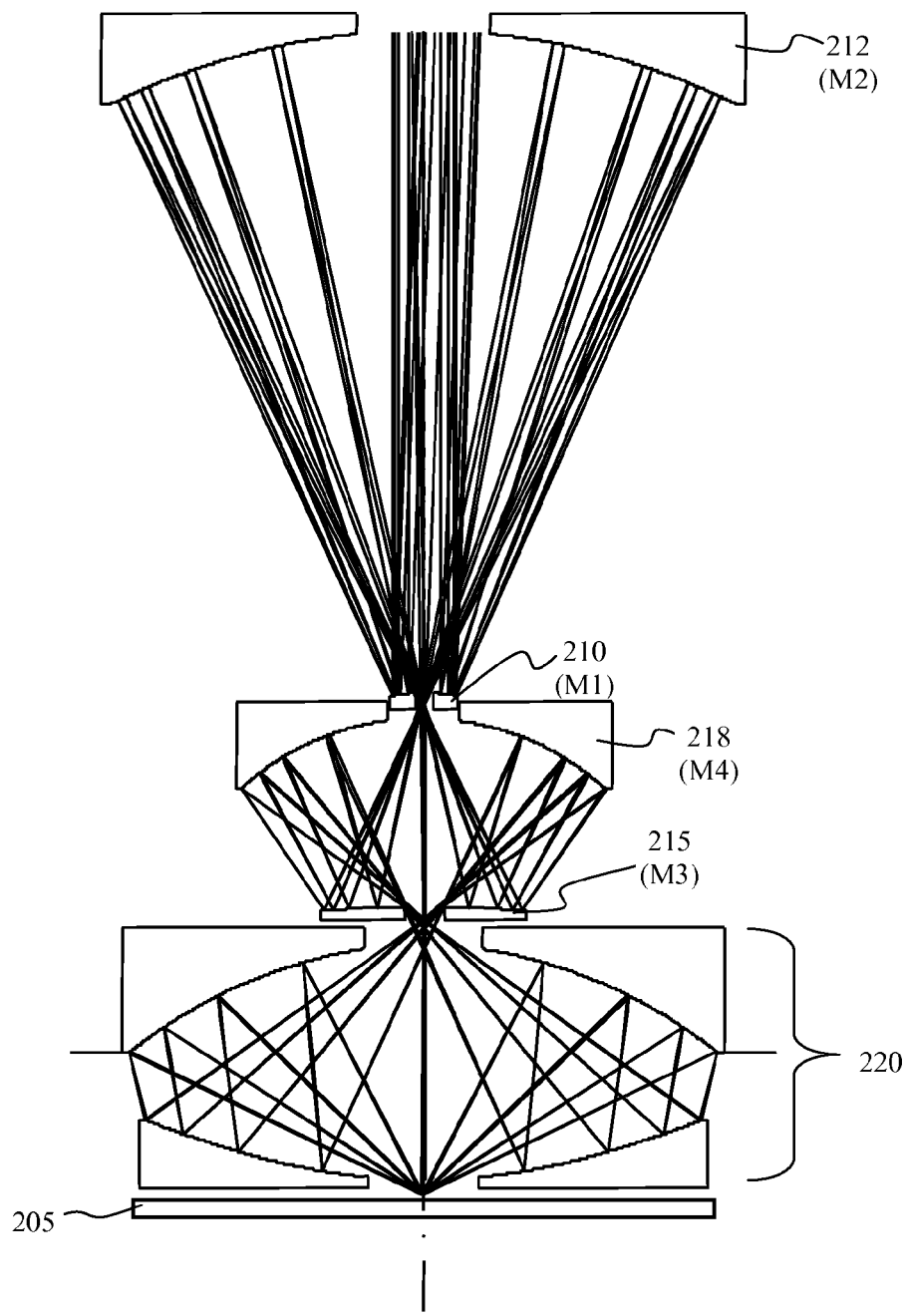
FIG. 2e illustrates a third example of an embodiment of an objective portion, which allows a curved Petzval field.

FIG. 2e illustrates a second example of an embodiment of the inventive system, which allows a curved Petzval field. FIG. 2f sets forth a possible example of dimensions and specifications for an objective of the type depicted in FIG. 2e. By allowing the curved Petzval field and using the objective with the refractive pupil relay as illustrated in FIG. 1c, the size of mirror 210 (M1 and the central obscuration can be further optimized.

The inventive optical systems, by utilizing multiple mirrors for proper aberration distribution, and utilizing aspheric surfaces to correct spherical aberrations, may be able to produce diffraction-limited imaging quality with NA greater than 0.7 and a field of view (FOV) greater than 0.5 mm, more preferably greater than 0.8 mm, still more preferably greater than 1 mm, while limiting central obscuration to about 35%. As used herein, the field of view refers to the size of the part of the sample that is being imaged. This may be defined as the size of the field for which the Strehl ratio is greater than 0.9.

The manufacturability of the objective, specifically the aspheric mirrors, can be further improved by shifting some of the spherical aberration to the refractive optics group and compensating by making one or more of the refractive lens surfaces into aspheric surfaces.

It is not intended that the invention be restricted to the exact embodiments described herein. Those skilled in the art will recognize that changes and modifications can be made without departing from the inventive concept. For example, the objective may include a front refractive element to seal off a central opening of the outermost mirror and another refractive module to provide the color correction.

Figure 3:
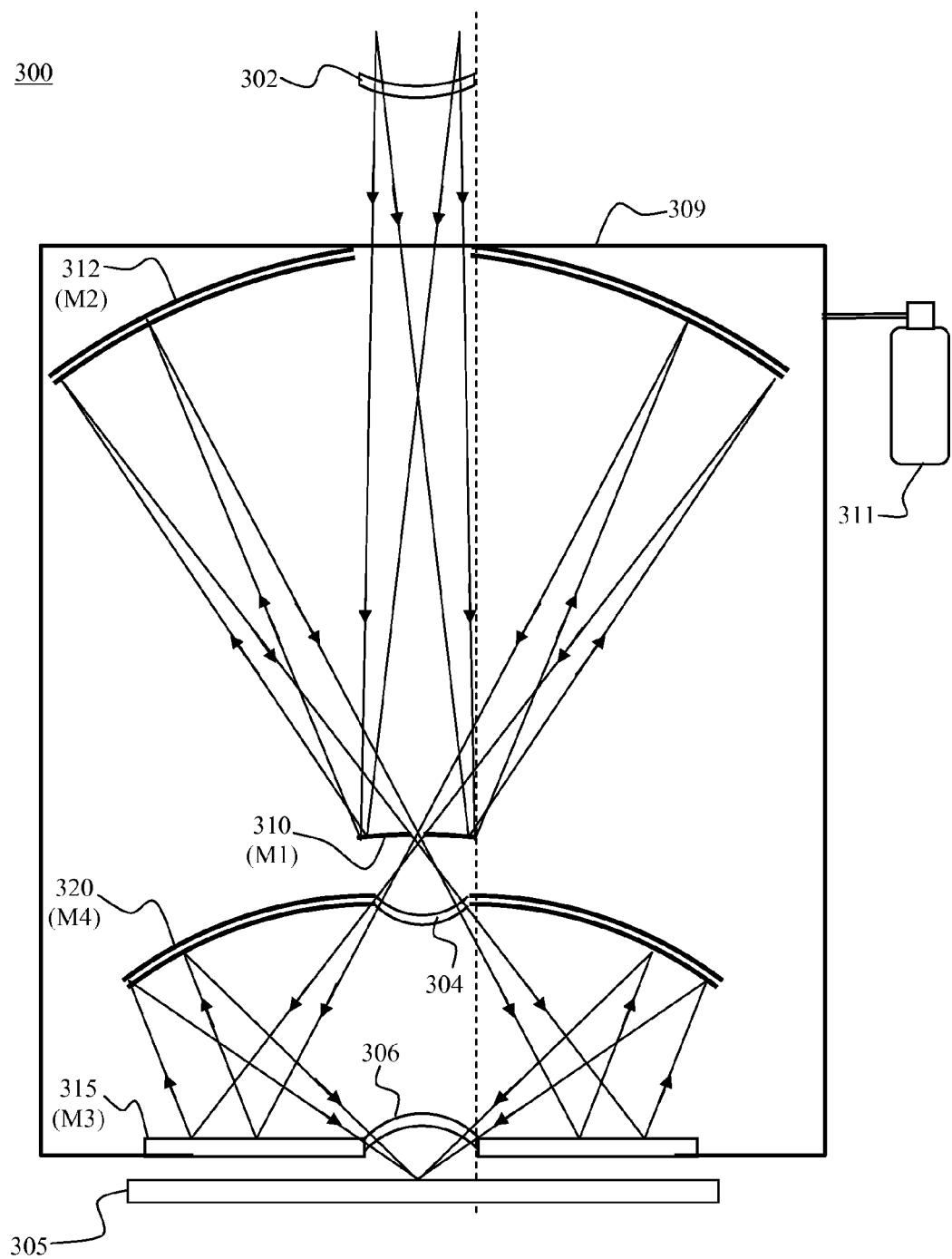
FIG. 3 illustrates an example of an embodiment of the invention in which the objective includes a curved front refractive element to seal off the central opening for the outermost mirror closer to the sample and another refractive module to provide corrections to color aberration caused by the front refractive element.

By way of example, an optical system of the type depicted in FIG. 1a may utilize an alternative objective 300 as shown in FIG. 3. The objective 300 includes curved mirrors 310 (M1), 312 (M2), 320 (M4) and a flat outermost mirror 315 (M3). Light enters or exits the objective via a first refractive lens 302 and an aperture in mirror 312 (M2), which lies between the first lens 302 and mirror 310 (M1). Taking the example of incident light traveling toward a sample 305, after passing through the first lens 302, the light is reflected from mirror M1 and then reflected by mirror 312 (M2) back through a central opening in mirror 310 (M1). The light then passes through a second lens 304 that is disposed in a central opening of mirror M4. After passing through the second lens 304, the light reflects from the outermost mirror 315 (M3). In this example, the reflecting surface of mirror 315 (M3) is a flat reflecting surface that faces away from the sample 305. The light reflected from mirror 315 (M3) is reflected by mirror 320 (M4) through a third lens 306 disposed in a central opening of mirror M3.

The mirrors 310 (M1), (312) M2, (315) M3, and 320 (M4) may be enclosed within a housing 309 to keep atmospheric contaminants out of the optical paths through the objective 300. Contaminants may be purged from beam paths by a purge gas delivered from a purge gas source 311. Typically, the purge gas is a dry inert gas with high purity, such as nitrogen or a noble gas. To protect a sample from contaminants that might be blown through the opening in the mirror 315 (M3) by the purge gas, the opening may be closed with a refractive optical module, such as lens 306. By way of example, but not bay way of limitation, the lens 306 may be a refractive spherical shell lens.

To reduce unwanted reflections, the surfaces of the refractive optical elements 302, 304, 306 the lenses 302, 304, 306 may be coated with anti-reflection coatings. As discussed above, the mirrors 310 (M1), 312 (M2), 315 (M3), 320 (M4) and lenses 302, 304, 306 may be configured in such a way that light passing through the lenses 302, 304, 306 is incident on the surfaces of the lenses at angles of incidence less than 25 degrees, more preferably, less than 10 degrees. The mirrors and lenses may be appropriately configured by a suitable choice of the radii of curvature diameters and positions of mirrors 310 (M1), 312 (M2), 315 (M3), 320 (M4), and lenses 302, 304, 306, the size of the central openings in mirrors 310 (M1), 312 (M2), 315 (M3) and 320 (M4), and the spacing between mirror 315 (M3) and the sample 305. By way of example, and not by way of limitation, the refractive element 306 at the outermost mirror 315 may be curved such that an angle of incidence of light on an optical surface of the refractive element 306 is less than about 25 degrees, more preferably less than about 10 degrees if ghost images are not a concern. As used herein, an optical surface refers to a surface at which light is refracted as it enters or leaves a lens. Such a low angle of incidence results in better anti-reflection performance from the optical surfaces of the refractive module. However, if ghost reflections are a concern, it may be desirable to increase the radius of curvature of the front element so ghost images (from the front element back to the sample) are highly defocused. Furthermore, the front refractive element 306 may be very close to flat to reduce the sensitivity to alignment error. Furthermore, a graded coating may be deposited on a surface of the refractive element to improve AR performance.

In addition, in some implementations, the second and third lenses 302 and 304 may implement color aberration correction to correct color aberration introduced by the first lens 306. For a broadband imaging system, and/or for an imaging system with spectrum below 270 nm or below 250 nm, or below 220 nm, the refractive module 306 may introduce excessive color aberration. To compensate for the color aberration, one or more additional refractive modules may be included inside the objective 300. Alternatively, downstream refractive optics, such as pupil a relay and zoom as discussed above, may be used to provide the color correction.

In some embodiments, the refractive module 306 may be configured to provide a field curvature that is opposite to the field curvature generated by the mirrors 310, 312, 315, 320. For example, if the mirrors produce a negative field curvature, the refractive optical element 306 may produce a positive field curvature and vice versa. The opposite field curvature of the refractive element 306 relaxes the aspect ratio requirements on the mirrors, particularly outermost mirror 315.

Furthermore, the refractive element 306 may be configured to provide an aberration balance for the mirrors 310, 312, 315, 320 to improve their manufacturability in terms of reduced aspheric departure and reduced aspect ratio. Specifically, a perfectly spherical reflecting surface typically exhibits optical aberrations, such as spherical aberration. Spherical aberration generally refers to a situation where a lens or mirror has different focal lengths for light rays incident at different height from the optical axis. A negative spherical aberration brings the marginal ray focus closer. To compensate for spherical aberration, a curved mirror is typically manufactured with a curvature that departs from being spherical and is more close to being paraboloidal. By way of example, and not by way of limitation, to reduce the amount of aspheric departure that is necessary, the refractive element 306 may have a refracting surface that departs slightly from spherical curvature in a way that compensates for at least part of the spherical aberration in one or more of the mirrors 310, 312, 315, 320.

In addition, for some implementations it may be desirable that the refractive elements be relatively flat. Generally speaking, a refractive element may be said to be flat if it has front and back refractive surfaces that characterized by an infinite radius of curvature. As used herein, a refractive element is said to be "nearly flat" if its front and back refractive surfaces are characterized by a radius of curvature greater than 500 mm. Flatter elements tend to be easier to manufacture and align and can be field replaced.

In some implementations, it may be desirable to make the refractive module 306 in the outermost mirror 315 field replaceable. By replaceable, it is meant that the refractive module 306 is designed to be removed from the outermost mirror 315 and easily installed. To make front refractive element field replaceable, the alignment sensitivity should be relatively loose in terms of axial and lateral alignment tolerances. By way of example, lateral and axial alignment tolerances in the range of a few microns are suitable for a replaceable refractive module 306.

Figure 4:
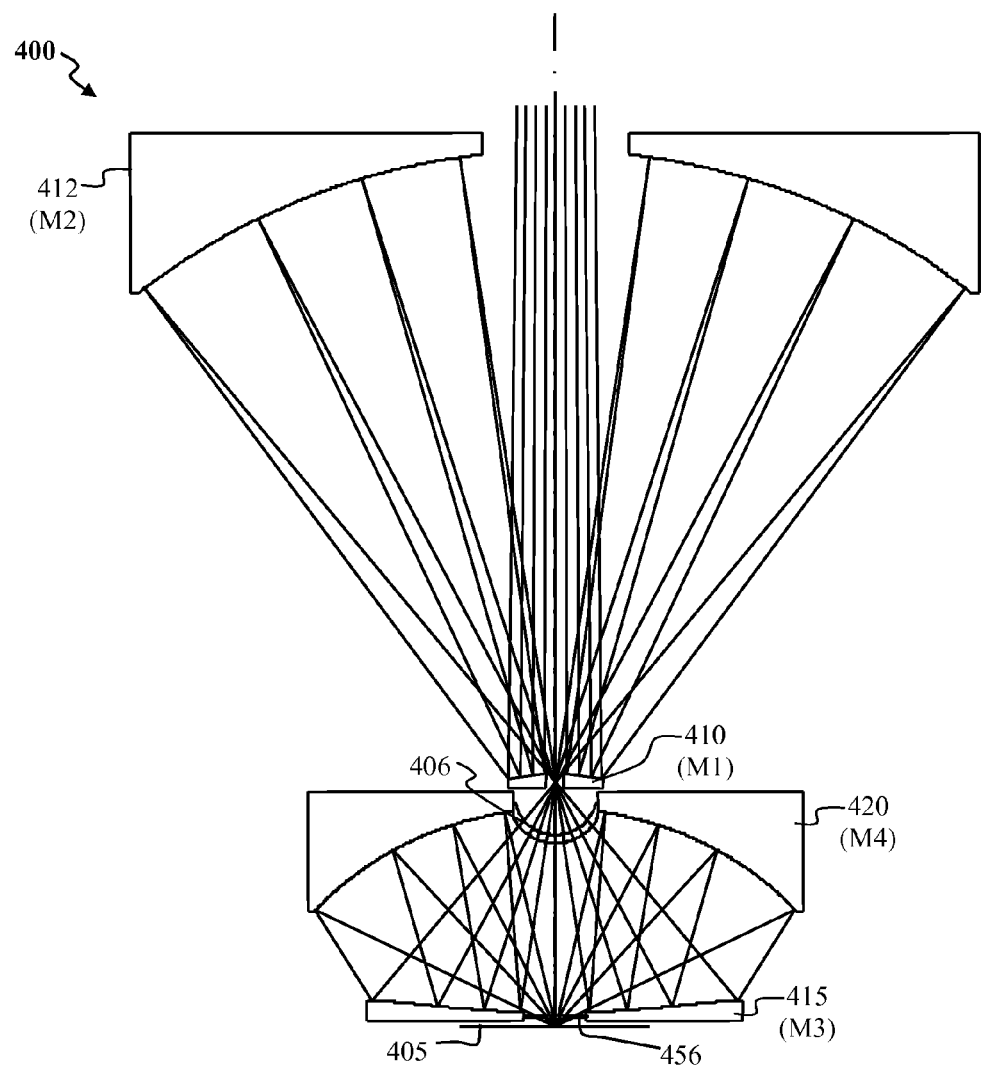
FIG. 4 illustrates an example of another embodiment of the invention in which the objective includes a flatter front refractive element to seal off the central opening for the outermost mirror closer to the sample and another refractive module to provide the color correction.

Although refractive modules based on curved refractive elements are shown and described above, embodiments of the present invention include implementations for which the refractive module includes a flat or nearly flat refractive element. FIG. 4 depicts an example of an objective 400 having a flat or nearly flat refractive element in an outermost mirror. The objective 400 generally includes mirrors 410 (M1), 412 (M2), 415 (M3), and 420 (M4). In this example, mirror 415 (M3) is the outermost mirror, i.e., the mirror closest to a target 405 when the objective is used in an imaging system. A flat or nearly flat refractive element 456 covers a central opening in the outermost mirror 415 (M3).

The objective 400 may include one or more additional refractive modules other than the refractive element 456. For example, as depicted in FIG. 4, a second refractive element 406 may cover a central opening in another of the mirrors, such as mirror 420 (M4).

There are a number of different configurations for the outermost mirror 115' in the objective. As seen in the second example depicted in FIG. 5, an outermost objective mirror element 500 may include a mirror body 502, which may be made of an optically transparent or an optically opaque material. A surface 501 of the mirror body 502 is coated with a reflective coating 504, except for an opening through a central portion of the mirror body. By way of example, the surface 501 may have a curved shape. The reflective coating 504 is on a surface of the mirror body that faces away from a sample 505 when the mirror element 500 is incorporated into an objective. A refractive element 508 is disposed in the aperture in such a way that the aperture is sealed against transmission of contaminants. The refractive optical element 508 may have a different curvature than the portion of the mirror body surface that is coated with the reflective coating. The refractive optical element 508 may include one or more concave or convex refracting surfaces to provide desired optical focusing properties. Alternatively, the refractive optical element 508 can include flatter optical elements that have graded optical coating to improve the AR efficiency.

Figure 5:
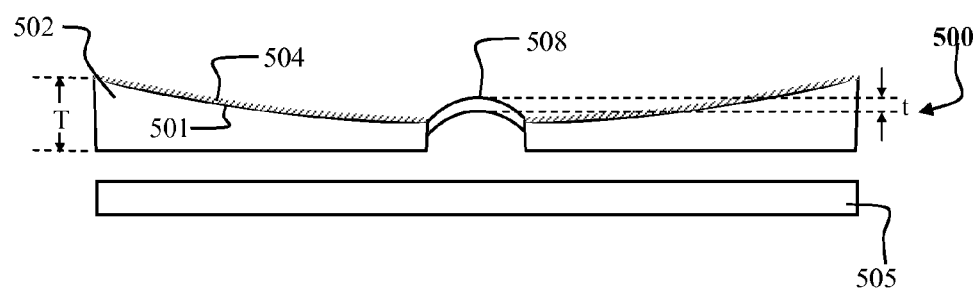
FIG. 5 illustrates an example of an outermost objective mirror element according to an embodiment of the present invention.

In the example depicted in FIG. 5, the mirror body is 502 in the shape of a disk having a central aperture. The mirror body 502 may have a thickness T at its outer edge. The refractive optical element 508 may have a thickness t that is less than the thickness T of the mirror body 502. This allows a thicker mirror body to be used, thereby simplifying manufacture of the optical element 500. By way of example, and not by way of limitation, mirror body and refractive element may be characterized by a thickness ratio T/t a between 2:1 and 4:1.

As discussed above, an optical imaging system, e.g., an imaging system used for defect inspection, may use an objective coupled with a pupil relay/variable magnification system that uses refractive optics. Further embodiments of the present invention are directed to extending the flexibility and adaptability of such optical systems are described below with respect to FIG. 6 to FIG. 9. The flexibility and adaptability of such an optical system may be extended by configuring the system so as to provide two or more imaging paths in the portion of the optical system external to the objective. This can enable simultaneous inspection, using multiple wavelength bands, and different modes (i.e., BF vs. DF), and/or using different pixel sizes. Additionally, two or more illumination paths may also be provided. One of the common components to such inventive configurations are independent pupils in the different imaging paths.

US Patent Publication No. US 2005/0052643 by Lange et al, which is hereby incorporated by reference, discloses a surface inspection method involving illuminating the surface in two optical regimes including a first wavelength range selected so that the surface is opaque to the light in the first wavelength range and a second wavelength range selected so that the surface is at least partially transmissive to light in the second wavelength range. Lange's method mentions separate illumination sources and multiple detection subsystems including multiple magnifications and brightfield vs. darkfield detection. Certain embodiments of the present invention provide improvements to Lange's method that enable simultaneous inspection with multiple illumination paths, multiple imaging paths, multiple wavelength bands, multiple magnifications, multiple modes, and combinations thereof using a common imaging objective.

Another advantage of splitting image collection from a single, ultra-broad-band objective into two image collection bands is that it enables the use of a refractive pupil relay and variable magnification optics. Advantages of using a refractive pupil relay in preference to a pupil relay composed of reflective elements are described above and in U.S. Provisional Application No. 60/997,306. These advantages include the higher efficiency of AR coatings used for refractive elements as compared to the HR coatings used for reflective elements. However, use of AR coatings for a broad wavelength spectrum such as 193 nm-450 nm wavelength, i.e., ranging from VDUV through DUV through UV, presents some serious challenges. There is a fairly wide range of AR materials which work well, i.e., at high efficiency and with low absorption, at the higher wavelength end of this range, i.e., approximately 250-450 nm wavelength, but do not function well at smaller wavelengths of the DUV range, i.e., they begin to have high absorption at shorter wavelengths. There is only a limited number of DUV AR materials that function well at the lower wavelength end of the range, i.e., approximately 193-250 nm wavelengths. A description of various coatings and their properties can be found in Materials for Optical Coatings in the Ultraviolet, F. Rainer, W. Howard Lowdermilk, D. Milam, C. K. Carniglia, T. T. Hart, and T. L. Lichtenstein, Applied Optics, Vol. 24,No. 4, 15 Feb. 1985,pg. 496 ff, the contents of which are incorporated herein by reference. Though these materials can function at the higher wavelengths as well as at the lower wavelengths, they are not the preferred materials to use for higher wavelengths for the following reasons: AR coatings are generally formed as a mixture of low-index and high-index layers, as described in Warren J. Smith "Modern Optical Engineering", 3rd Edition, McGraw-Hill, Inc., Chapter 7: Optical Materials and interference Coatings. Among the materials used for the short wavelength DUV coatings, the high index materials, such as $Al_2O_3$ do not have as high an index as desired, i.e., the index spread is not as great between the low and high index materials. This requires more layers for the AR coating, and is harder to design. Additionally, the coating process for the DUV AR materials suitable for the short wavelength end of the DUV range is not as robust as the coating process for the materials used at the higher wavelength end of the range.

For the above reasons, limiting DUV AR materials to a narrower bandwidth than the entire 193-450 nm range can decrease the associated design difficulties.

An aspect of the following embodiments of the present invention is enabling simultaneous inspection of two wavelength bands. By way of example, and not by way of limitation, these two wavelength bands may include a first band containing wavelengths less than 250 nm and a second wavelength band from about 250 nm to approximately 450 nm, up to the visible range. In this way, the optimal AR materials may be used for each wavelength sub-range, while maintaining high throughput by means of the simultaneous inspection. This division of wavelength bands has a fundamentally different motivation than the division of wavelength bands described by Lange in Publication No. US 2005/0052643. The division detailed by Lange is at approximately 350 nm, in the region where the division between opacity and transmissivity tends to occur for commonly used materials in semiconductor fabrication such as polysilicon and high-K dielectrics.

Figure 6:
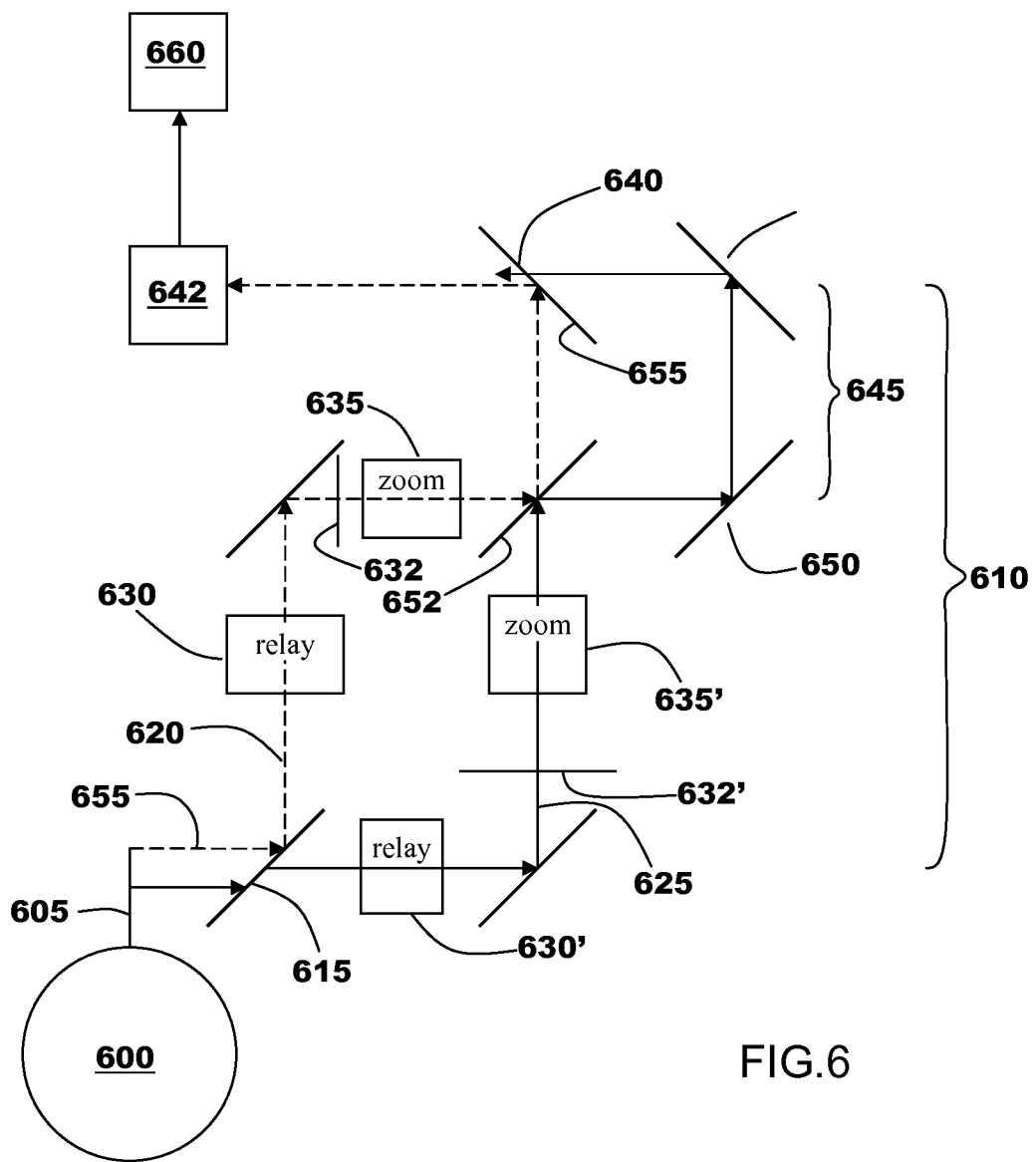
FIG. 6 illustrates an exemplary embodiment of the portion of an optical system external to the objective portion, which is configured for simultaneous inspection over two wavelength bands.

FIG. 6 illustrates an exemplary embodiment of the portion of an optical system external to the objective portion, which is configured for simultaneous inspection over two wavelength bands. It is noted that the particular details of the configuration may be modified. Objective 600 may be a catoptric objective as in any of the embodiments described above, e.g., with respect to FIG. 1*b*, FIG. 2*b*, FIG. 2*e*, FIG. 3, and FIG. 4 and previously incorporated U.S. provisional patent application No. 60/997,306. Outgoing light 605 from objective 600 enters an imaging system 610 that includes two or more pupil relay/variable magnification modules. A 50/50 beam splitter 615 reflects light with wavelength shorter than a predetermined value, 250 nm for example, and transmits light with wavelength longer than the predetermined value. The beam splitter 615 acts as a long-pass filter, i.e. HT (High Transmission) for DUV and visible light, HR (high reflectance) for VDUV. The outgoing light 605 collected by the objective 600 is therefore routed into two paths; path 620 for the shorter wavelength light, path 625 for the longer wavelength light. Each path includes: a) pupil relays (630 for path 620, 630' for path 625), which may be comprised of refractive elements and be configured as described above and as disclosed in U.S. patent application No. 60/997,306. The refractive elements used in pupil relay 630 employ VDUV AR coatings suitable for the 190-250 nm (or 190-270 nm) wavelength band, the refractive elements used in pupil relay 630' employ DUV/UV AR coatings suitable for the 250-450 nm (or 270-450 nm) wavelength band; b) pupils 632 and 632'; c) zoom/variable magnification modules (635 for path 620, 635' for path 625). The AR coatings for the zoom/variable magnification refractive elements are employed for paths 620 and 625 similarly to the pupil relay elements for the two paths. The two paths re-converge at point 640 and may continue to a shared module 642, which may be a long range optical trombone module to provide optical path adjustment for a large magnification range. As used herein, an optical trombone (or sometimes simply a trombone) refers to an arrangement of two or more optically reflecting surfaces in which displacement of one or more of the reflecting surfaces along a direction parallel to an optical path varies a length of the optical path. An example of a long range trombone is described in U.S. Pat. No. 6,801,357, issued Oct. 5, 2004, the entire contents of which are incorporated herein by reference. An additional trombone module 645 may be inserted, using HR mirrors 650, into one of the paths to account for the path length difference between the two paths. In the example depicted in FIG. 6, mirror 652 is two-sided HR: one side for VUV, the other side for DUV/VIS. However, this should not be construed as a limitation on all embodiments of the invention. Independent zoom modules 635 and 635' provide fine zoom control. Long-pass filter 655 provides for the re-convergence of the two paths. The reconverged paths continue through the shared module 642 and are directed onto sensors 660. In a preferred embodiment, sensors 660 are TDI (Time Delayed Integration) sensors. A description of TDI can be found at www.learn.hamamatsu.com/tutorials/tdiscan.

Figure 7:
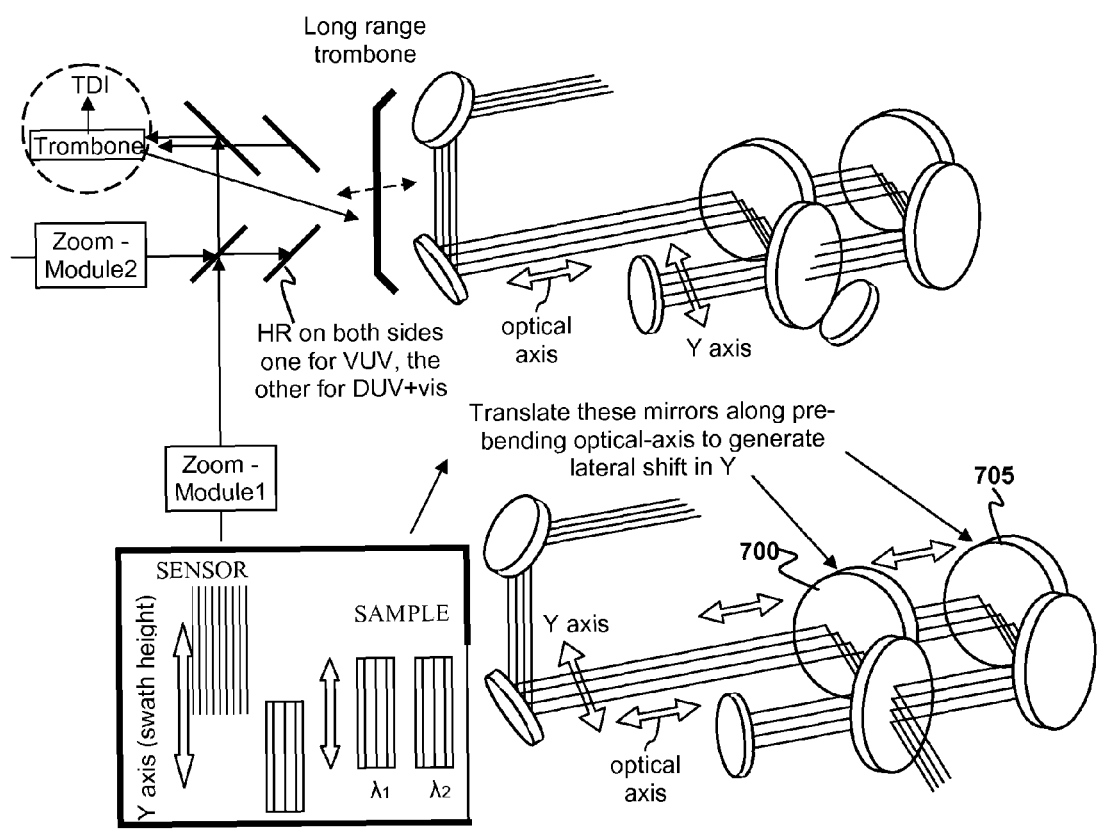
FIG. 7 illustrates a sub-portion of FIG. 5, including the mirrors used to generate a lateral shift between the two wavelength bands.

When two distinct wavelength bands are used, the field on the sample can be slightly different for the two wavelengths for more efficient usage of the objective FOV. This results in a slight offset between the images of the two wavelengths as the signal is transmitted to the sensors, which can enable the use of different sensors for the different wavelength bands. (FIG. 7 illustrates how the offset can be adjusted, by translating mirrors 700 and/or 705 along the optical axis to generate a lateral shift in y. This allows the sensors to be chosen to optimize the efficiency, according to the specific configurations of the imaging paths. This will be illustrated hereinafter in FIG. 9 which lists some exemplary sensor utilization options.

An aspect of these particular embodiments of the present invention is enabling the collection of simultaneous inspection with bright field (BF) and dark field (DF) images in different spectrums. BF modes collect specularly reflected light, whereas DF modes detect scattered light, but not specularly reflected light. In DF detection, therefore, specularly reflected light is blocked out. In many cases for DF modes, diffraction lobes from light scattered by regular patterns on the sample are also blocked out using opaque structures (called pupil filters) placed in the image pupil. By way of example and not by way of limitation, the pupil filters may include one or more Fourier filters.

Consequently, for DF inspection, the accessible pupil, where the blocking takes place, cannot be in a common path with illumination, in order to avoid obscuration of the illuminating light by the pupil filtering. This is not the case for BF inspection, where specularly reflected light is not blocked at the pupil. If the pupil relay elements are refractive rather than reflective, as described above and in U.S. provisional patent application No. 60/997,306, the pupil relay can be in a common path with the illumination, in contrast to the pupil itself in the DF case. Due to the required blocking present in the accessible pupil for DF, in order to have two simultaneous different imaging modes such as BF and DF, two independent pupils are required. The associated pupil relays may be shared or independent, depending on the other considerations and constraints for the system. For example, in order to split the output of a single pupil relay into multiple paths containing multiple pupils, there would need to be sufficient distance between the last optical element of the pupil relay and the pupils for the mechanical packaging of the folding mirror, B.S., pupil mechanism, etc.

Another aspect of the embodiments of the present invention described with respect to FIG. 6 to FIG. 9 is the incorporation of dual variable magnification modules so as to enable use of both high resolution wafer pixels, i.e., about 40 nm, and high throughput wafer pixels, i.e., about 250 nm, so as to image onto sensor pixels. By way of example and not by way of limitation, the sensor pixels may be may be about 18 microns (μm) in dimension.

A further aspect of the embodiments of the present invention described with respect to FIG. 6 to FIG. 9 is the capability of incorporating a plurality of illumination paths in addition to the plurality of imaging paths. This may be beneficial in that the spectrum, output power, and configuration can be independently chosen and adjusted for the different bands. Different illumination settings could also be used. The illumination configuration includes the numerical aperture, the illumination aperture, the polarization, the light power, and the illumination location on the sample.

Figure 8:
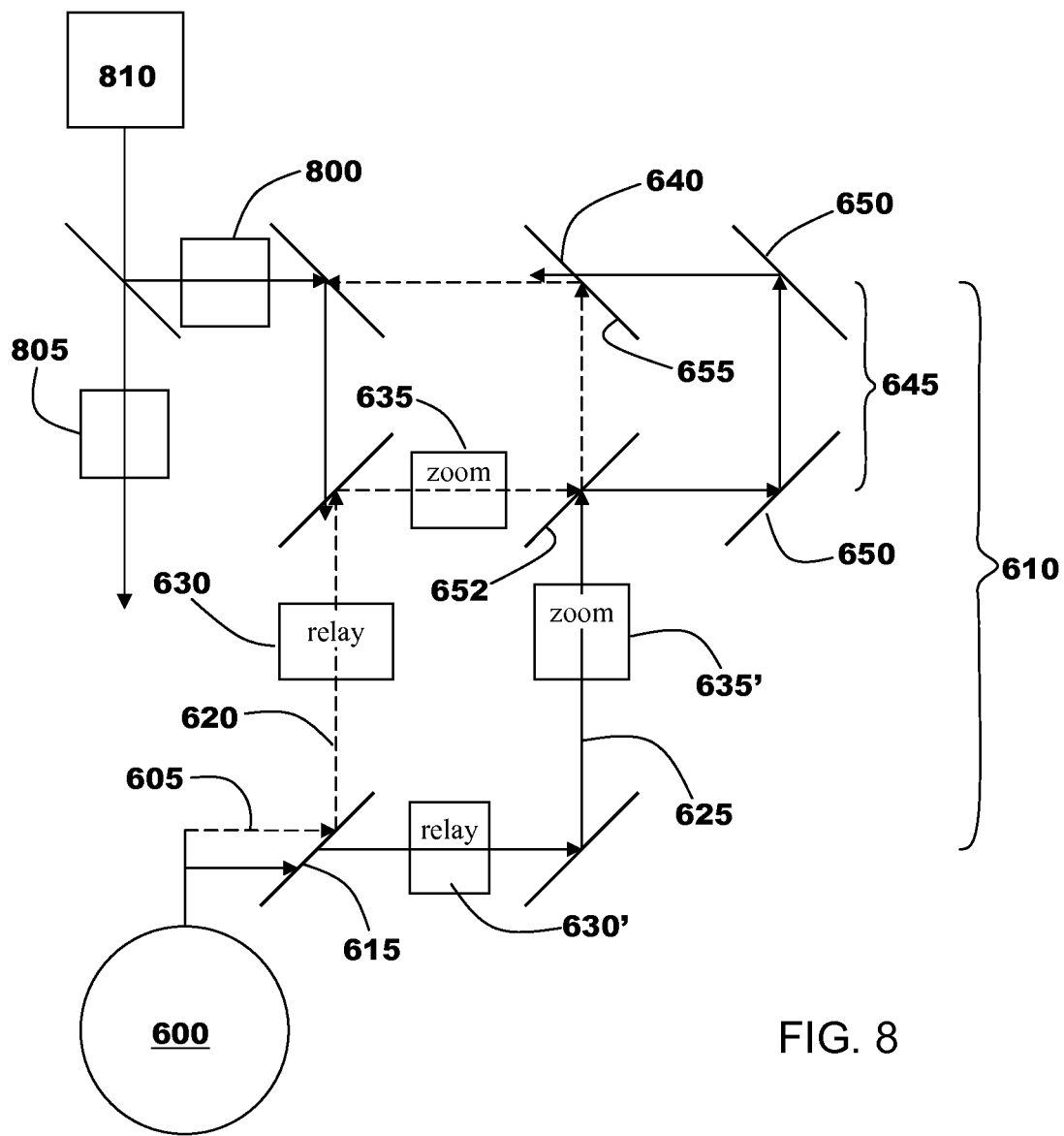
FIG. 8 illustrates an example of a configuration of the inventive optical system employing dual illumination paths.

An example of a configuration employing dual illumination paths is illustrated in FIG. 8.

The configuration in FIG. 8 is similar to that depicted in FIG. 6, except that separate illuminator modules 800 and 805 can be employed in the two paths, and separate illuminators could be utilized in place of single source 810. The rest of the components of the configuration depicted in FIG. 8 operate as described above with respect to FIG. 6.

Figure 9:
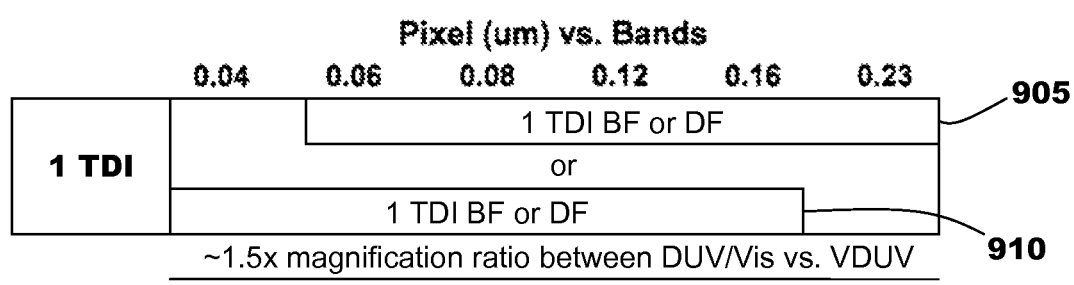
FIG. 9 illustrates some examples of sensor utilization configurations, and how they might be utilized with different wavelength spectra and modes.

An aspect of the present invention is the flexibility of designing an illumination/imaging configuration which enables simultaneous inspection with choices of several of the above-mentioned parameters. FIG. 9 illustrates some examples of sensor utilization configurations, and how they might be utilized with different wavelength spectra and modes. Top row 905 illustrates configurations for the DUV/Vis spectrum; bottom row 910 illustrates configurations for the VDUV band. The magnification setting and range of the zoom can be different between these two paths.

The embodiments of the present invention described above with respect to FIG. 6 to FIG. 9 extend the flexibility and adaptability of current optical systems by providing two or more imaging paths having separate, independent pupils, in the portion of the optical system external to the objective. This can enable inspection, which may be simultaneous inspection, using multiple wavelength bands, using different modes (e.g., BF vs. DF), and/or using different magnifications to map into different pixel sizes. In general, modes could be independently set in both imaging paths by constructing apertures in both illumination and collection pupils of each imaging path (band). These apertures control the collection of angles used to illuminate and collect image data in such a way as to optimize or vary the defect contrast, patter contrast and scattered light "noise" from the sample. Additionally, two or more illumination paths may also be provided. Furthermore, we propose that the system can be configured so that the pixel size of the two imaging paths can be adjusted independently and the line data (rate at which TDI array lines are digitized) of two TDI sensors can be set differently, so that $$(\text{pixel size} \times \text{line rate})_{path1} = (\text{pixel size} \times \text{line rate})_{path2} = \text{stage speed}$$

Larger pixel size (at the sample) can be achieved by either changing the magnification of one of the imaging path and using identical sensors or by keeping magnification constant for both paths and employing a sensor with larger pixel area in one of the two paths. Thus, the system allows simultaneous two-mode inspection with different pixel sizes. For example, to optimize inspection sensitivity, light-budget and throughput BF inspection may be done with smaller pixel size, while DF inspection may be done with larger pixel size. Furthermore, this strategy can be applied to other types of imaging systems such as spot scanning systems.

Those skilled in the art will recognize that modifications can be made to the exact embodiments disclosed herein without departing from the inventive concept. For example, other types of objectives, and other types of sensors may be utilized. The scope of the invention should be construed in view of the claims.

While the above is a complete description of the preferred embodiment of the present invention, it is possible to use various alternatives, modifications, and equivalents. Therefore, the scope of the present invention should be determined not with reference to the above description but should, instead, be determined with reference to the appended claims, along with their full scope of equivalents. Any feature, whether preferred or not, may be combined with any other feature, whether preferred or not. In the claims that follow, the indefinite article "A", or "An" refers to a quantity of one or more of the item following the article, except where expressly stated otherwise. The appended claims are not to be interpreted as including means-plus-function limitations, unless such a limitation is explicitly recited in a given claim using the phrase "means for."

What is claimed is:

1. An optical system for sample inspection comprising: an objective comprising at least four mirrors including an outermost mirror; and focusing optics optically coupled to the objective, wherein the focusing optics include one or more refractive optical elements, wherein the at least four mirrors are configured to provide the objective with imaging at a numerical aperture greater than 0.7, central obscuration less than 35% in pupil, and wherein an aspect ratio of outermost mirror at a sample side is no more than 20:1.

2. The optical system of claim 1 wherein the focusing optics include a relay module configured to relay an aperture stop inside the objective to a pupil plan located outside the objective.

3. The optical system of claim 1 wherein the focusing optics are configured to provide variable magnification.

4. The optical system of claim 1, further comprising a refractive element disposed in a central opening in an outermost mirror of the objective to seal off a central obscuration at the outermost mirror.

5. The optical system of claim 4, further comprising one or more additional refractive elements inside the objective, wherein the one or more additional refractive elements are configured to provide color correction for the refractive element disposed in the central opening in the outermost mirror.

6. The optical system of claim 1 wherein objective is characterized by a negative field curvature.

7. The optical system of claim 6, wherein the focusing optics are characterized by a Petzval curvature that compensates for the field curvature of the objective.

8. The optical system of claim 1 wherein the objective is characterized by a sample field size that is greater than 0.5 mm.

9. The optical system of claim 1 wherein the objective includes six mirrors and is configured to provide imaging of infinite conjugate.

10. The optical system of claim 9 wherein objective includes an outermost mirror module that generates an intermediate field characterized by negative spherical aberration.

11. The optical system of claim 10 wherein the objective includes more than one convex mirror.

12. The optical system of claim 1, further comprising one or more optical elements configured to compensate for optical aberrations between the objective and the focusing optics.

13. An imaging objective, comprising:
six mirrors, at least one of which contains a refractive module that seals off a central opening of an outermost mirror of the six mirrors in order to substantially isolate an atmosphere inside the objective from a sample atmosphere, wherein said six mirrors include a two-mirror relay group adjacent a convex mirror, the two-mirror relay group including the outermost mirror and another mirror disposed between the convex mirror and the outermost mirror, wherein said two-mirror relay group has a magnification close to one, and wherein said two-mirror relay group has a negative spherical aberration, wherein said objective is infinite conjugate; and said objective has a flat Petzval field.

14. The imaging objective of claim 13 wherein the refractive module and one or more mirrors are configured such that light passing through the objective is incident on an optical surface of the refractive module at an angle of incidence that is less than about 25 degrees.

15. The imaging objective of claim 13 wherein the refractive module includes an optical element that is flat or nearly flat.

16. The imaging objective of claim 13 wherein the refractive module is configured to provide a field curvature that is opposite to the field curvature generated by the two or more mirrors.

17. The imaging objective of claim 13 wherein the refractive optical element is configured to compensate for an optical aberration of one or more of the one or more mirrors.

18. The imaging objective of claim 13 wherein the two or more mirrors includes one or more mirrors, other than the outermost mirror, having a body with a central opening and a refractive optical element disposed in the central opening.

19. The imaging objective of claim 18 wherein the refractive optical element is configured to provide color correction.

20. The imaging objective of claim 13 wherein the two or more mirrors include at least four mirrors.

21. The imaging objective of claim 13, wherein said negative spherical aberration is less than two times a distance between a reflective surfaces of the relay mirror and a reflective surface of the convex mirror.

22. A optical imaging system comprising a single objective and two or more broadband imaging paths optically coupled to the objective, wherein the objective and imaging paths are configured to provide broadband imaging at a numerical aperture greater than 0.7 and a field of view greater than 0.8 mm, at least one of said imaging paths includes a long range optical trombone, wherein the optical trombone includes an arrangement of two or more optically reflecting surfaces in which displacement of one or more of the reflecting surfaces along a direction parallel to an optical path varies a length of the at least one optical path.

23. The system of claim 22 wherein each of said two or more imaging paths contains a separate independently accessible pupil.

24. The system of claim 23 wherein the two or more imaging paths are configured to enable simultaneous inspection of a surface of a sample proximate the objective with a plurality of inspection modes.

25. The system of claim 24 wherein said plurality of inspection modes comprises a bright field mode and a dark field mode.

26. The system of claim 25 wherein said plurality of inspection modes comprises two different wavelength bands each wavelength band having a field on the sample and resulting in an image transmitted to a sensor.

27. The system of claim 26, further comprising different sensors coupled to each of said two or more imaging paths for detecting said different wavelength bands.

28. The system of claim 26 wherein said two different wavelength bands include a first band characterized by vacuum wavelengths less than about 250 nm; and a second band characterized by vacuum wavelengths between about 250 nm and about 450 nm.

29. The system of claim 26 wherein said two different wavelength bands include a first band that is at least 10 nm wide and includes vacuum wavelengths less than 250 nm.

30. The system of claim 29 wherein said two different wavelength bands further include a second band that is greater than 100 nm wide.

31. The system of claim 29, wherein said pupil relay is comprised of refractive elements.

32. The system of claim 31, wherein a single pupil relay is shared between a plurality of said imaging paths.

33. The system of claim 31, wherein each of said two or more imaging paths has a separate pupil relay.

34. The system of claim 26 wherein said two different wavelength bands include a first band that is at least 10 nm wide and includes vacuum wavelengths less than 270 nm.

35. The system of claim 34 wherein the optical components of the imaging paths include one or more refractive optical elements downstream of a split between the two imaging paths.

36. The system of claim 22 wherein the objective comprises at least four mirrors including an outermost mirror, wherein the objective is configured to provide imaging at a numerical aperture greater than 0.7, central obscuration less than 35% in pupil, and wherein an aspect ratio of outermost mirror at a sample side is no more than 20:1.

37. The system of claim 22 wherein the objective comprises two or more mirrors, at least one of which contains a refractive module that seals off a central opening of an outermost mirror of the two or more mirrors in order to substantially isolate an atmosphere inside the objective from a sample atmosphere.

38. The system of claim 22, wherein each of said two or more imaging paths includes: a pupil relay; a pupil; and a zoom/variable magnification module.

39. The system of claim 22, wherein each of said two or more imaging paths includes a variable magnification module operable to provide a plurality of magnifications that map into a plurality of pixel sizes.

40. The system of claim 22, wherein said two or more imaging paths have independent alignment and magnification adjustment.

41. The system of claim 22, wherein each of said imaging paths includes a sensor having a data rate, and wherein said data rate of each said sensor can be set independently.

42. The system of claim 22, further including a plurality of illumination paths.

43. The system of claim 42, wherein an optical spectrum, output power, and illumination configuration are independently chosen and adjusted for each of said illumination paths.

44. The system of claim 43, wherein said illumination configuration includes: numerical aperture, illumination aperture, polarization, light power, and illumination location on the sample.

45. An optical imaging system, comprising an objective configured to collect light from a sample located proximate the objective and two or more imaging paths optically coupled to the objective, wherein the two or more imaging paths are configured to provide a corresponding two or more simultaneous images of the sample in a corresponding two or more modes including a bright field mode in which specularly reflected light is collected and a dark field mode in which scattered light is collected but not specularly reflected light, wherein each mode of the two or more modes is characterized by an illumination pupil aperture and/or a collection pupil aperture and wherein each of the two or more simultaneous images is a broad band image.

46. An optical imaging system, comprising an objective configured to collect light from a sample located proximate the objective and two or more imaging paths optically coupled to the objective, wherein the two or more imaging paths are configured to provide a corresponding two or more simultaneous images of the sample in a corresponding two or more modes including a bright field mode in which specularly reflected light is collected and a dark field mode in which scattered light is collected but not specularly reflected light, wherein each mode of the two or more modes is characterized by a different pixel size at the sample.

47. A optical imaging system comprising a single objective and two or more imaging paths optically coupled to the objective, wherein the imaging paths are configured to transmit two different wavelength bands to one or more sensors, wherein the objective and optical elements that make up the imaging paths are configured to produce a slight offset between images of a sample at the one or more sensors for the two different wavelength bands, which can enable the use of different sensors for the different wavelength bands wherein at least one wavelength band is a broadband wavelength band having a wavelength bandwidth greater than 10 nm, wherein illumination for the two different wavelength bands is coupled to a sample through the objective, wherein the objective and imaging paths are configured to provide imaging at a numerical aperture greater than 0.7 and a field of view greater than 0.8 mm.

* * * * *